(12) United States Patent
Gessner et al.

(10) Patent No.: US 7,750,556 B2
(45) Date of Patent: Jul. 6, 2010

(54) TRIAZOLE DERIVATIVES AND USE THEREOF IN ORGANIC LIGHT-EMITTING DIODES (OLEDS)

(75) Inventors: Thomas Gessner, Heidelberg (DE);
Christian Lennartz, Schifferstadt (DE);
Hans-Werner Schmidt, Bayreuth (DE);
Mukundan Thelakkat, Bayreuth (DE);
Markus Baete, Kulmain (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 619 days.

(21) Appl. No.: 10/594,132

(22) PCT Filed: Mar. 14, 2005

(86) PCT No.: PCT/EP2005/002697

§ 371 (c)(1),
(2), (4) Date: Sep. 25, 2006

(87) PCT Pub. No.: WO2005/093007

PCT Pub. Date: Oct. 6, 2005

(65) Prior Publication Data

US 2007/0188078 A1    Aug. 16, 2007

(30) Foreign Application Priority Data

Mar. 23, 2004    (DE) .................. 10 2004 014 534

(51) Int. Cl.
*H01J 1/62*     (2006.01)
*H01J 63/04*    (2006.01)
*H01L 35/24*    (2006.01)
*H01L 51/00*    (2006.01)
*C07D 471/00*   (2006.01)
*C07D 487/00*   (2006.01)
*C07D 491/00*   (2006.01)

(52) U.S. Cl. .................. 313/504; 257/40; 544/254

(58) Field of Classification Search .................. None
See application file for complete search history.

(56) References Cited

U.S. PATENT DOCUMENTS

| | | | |
|---|---|---|---|
| 3,817,990 A | 6/1974 | Strobel, et al. |
| 4,157,443 A | 6/1979 | Fletcher |
| 4,739,053 A | 4/1988 | Albert et al. |

FOREIGN PATENT DOCUMENTS

| | | |
|---|---|---|
| DE | 25 54 027 | 6/1976 |
| DE | 27 49 902 | 5/1978 |
| DE | 30 01 424 | 7/1980 |
| DE | 3 304 330 | 8/1984 |
| EP | 0 704 436 | 4/1996 |
| EP | 0 710 655 | 5/1996 |
| EP | 0 875 947 | 11/1998 |
| EP | 1 026 222 | 8/2000 |
| WO | 03 105538 | 12/2003 |

OTHER PUBLICATIONS

Matsumoto, et. al., Heterocycles, (2003), 60(12) 2677-2684.*
Dorwald F. A. Side Reactions in Organic Synthesis, 2005, Wiley: VCH, Weinheim p. IX of Preface.*
Narita Shigeru, et al., "Application of Fluorescent Triazoles to Analytical C Hemistry. I. Determination of Aromatic Primary Amine With 2, 4, 6- Triaminopyrimidine as a Reagent", Chemical and Pharmaceutical Bulletin, vol. 33, No. 11, XP 008049633, pp. 4928-4934, 1985.

* cited by examiner

*Primary Examiner*—James O Wilson
*Assistant Examiner*—Jeffrey H Murray
(74) *Attorney, Agent, or Firm*—Oblon, Spivak, McClelland, Maier & Neustadt, L.L.P.

(57) ABSTRACT

The present invention relates to the use of triazole derivatives selected from the group consisting of triazolopyrimidine derivatives and triazolouracil derivatives in organic light-emitting diodes (OLEDs), an OLED comprising at least one of the organic triazole derivatives mentioned, a light-emitting layer comprising at least one of the triazole derivatives mentioned, an OLED comprising the light-emitting layer of the invention, a device comprising an OLED according to the invention and also specific novel triazole derivatives.

4 Claims, No Drawings

TRIAZOLE DERIVATIVES AND USE THEREOF IN ORGANIC LIGHT-EMITTING DIODES (OLEDS)

BACKGROUND OF THE INVENTION

Field of the Invention

The present invention relates to the use of triazole derivatives selected from the group consisting of triazolopyrimidine derivatives and triazolouracil derivatives in organic light-emitting diodes (OLEDs), an OLED comprising at least one of the organic triazole derivatives mentioned, a light-emitting layer comprising at least one of the triazole derivatives mentioned, an OLED comprising the light-emitting layer of the invention, a device comprising an OLED according to the invention and also specific novel triazole derivatives.

Organic light-emitting diodes (OLEDs) exploit the ability of particular materials to emit light when they are excited by means of an electric current. OLEDs are of particular interest as alternatives to cathode ray tubes and liquid crystal displays for producing flat VDUs. Owing to their very compact construction and their intrinsically low power consumption, devices comprising OLEDs are particularly useful for mobile applications, for example for applications in mobile telephones, laptops, etc.

Numerous materials have been proposed for use in OLEDs. The use of specific triazole derivatives in OLEDs has likewise been mentioned in the past.

EP-A 0 710 655 relates to green-emitting benzotriazole-metal complexes for use in light-emitting elements. The benzotriazole-metal complexes used have the following formula:

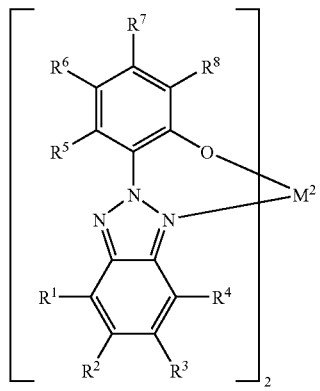

EP-A 0 875 947 relates to blue-emitting organic LEDs having oxadiazole, thiadiazole or triazole derivatives in the electroluminescent layer. These derivatives have the following formula:

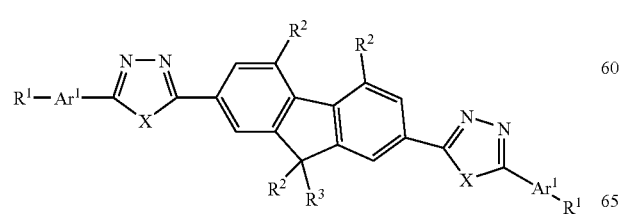

EP-A 0 704 436 relates to triazole derivatives and organic electroluminescent elements produced therefrom. The triazole derivatives have the following formula:

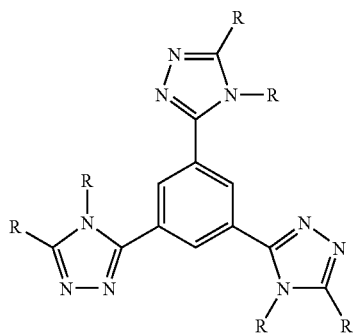

The triazole derivatives are preferably used in the electron transport layer. However, variation of the radicals can make the triazole derivatives also suitable in principle for light-emitting materials.

The abovementioned triazole derivatives are specific compounds, and the use of triazolopyrimidine derivatives and triazolouracil derivatives in OLEDs is not mentioned.

Triazolopyrimidine derivatives and triazolouracil derivatives are already known in the prior art.

Thus, DE-A 30 01 424 relates to v-triazolyl[4,5-d]pyrimidines of the general formula

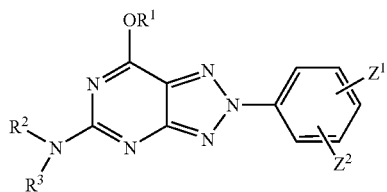

DE-A 27 49 902 likewise relates to v-triazolyl[4,5-d]pyrimidines. These compounds have the general formula

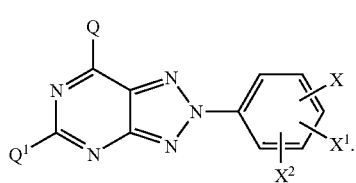

DE-A 25 54 027 relates to triazolyl compounds of the general formula

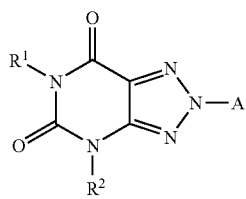

where A is a substituted phenyl radical.

In the dissolved or finely divided state, the compounds disclosed in DE-A 30 01 424, DE-A 27 49 902 and DE-A 25 54 027 display a more or less pronounced fluorescence and can be used for the optical brightening of organic materials.

None of the three abovementioned documents relates to electroluminescence of the triazole derivatives disclosed or their use in OLEDs.

WO 03/105538 relates to 2H-benzotriazoles and their use in organic light-emitting diodes. The benzotriazoles have at least one 2H-benzotriazole unit of the following formula:

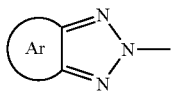

where Ar can be an aryl or heteroaryl radical. Although the basic structure of triazolopyrimidine derivatives is mentioned, inter alia, in WO 03/105538, there is no indication of specific substituents.

Although compounds which display electroluminescence in the blue, red and green regions of the electromagnetic spectrum are already known, the provision of further compounds is desirable. For the purposes of the present invention, the term electro-luminescence encompasses both electrofluorescence and electrophosphorescence.

It is therefore an object of the present patent application to provide compounds which are suitable for producing electroluminescence in the visible region of the electro-magnetic spectrum, in particular in the blue to blue-green region.

BRIEF SUMMARY OF THE INVENTION

This object is achieved by the use of triazole derivatives selected from the group consisting of triazolopyrimidine derivatives containing at least one substituent selected from the group consisting of OH, O-alkyl, O-aryl, halogen and amino and triazolouracil derivatives in organic light-emitting diodes (OLEDs).

It has been found that the triazolopyrimidine derivatives having at least one substituent selected from the group consisting of OH, O-aryl, halogen and amino and triazolouracil derivatives display electroluminescence in the visible region of the electromagnetic spectrum and can thus be used as emitter molecules in OLEDs.

The present invention therefore further provides for the use of the triazolopyrimidine derivatives and triazolouracil derivatives according to the present patent application as emitter molecules in OLEDs.

It is likewise possible to use the triazolopyrimidine derivatives and triazolouracil derivatives according to the present patent application as host molecules (matrix) in the emitter layer.

The present invention therefore further provides for the use of the triazolopyrimidine derivatives and triazolouracil derivatives according to the present patent application as host molecules (matrix) in the emitter layer.

Furthermore it is conceivable to use the specified triazole derivatives in other layers of an OLEDs, for example in the electron transport layer.

The triazole derivatives used according to the invention are preferably selected from the group consisting of triazolopyrimidine derivatives and triazolouracil derivatives selected from among compounds of the structural formulae I, II, III and IV:

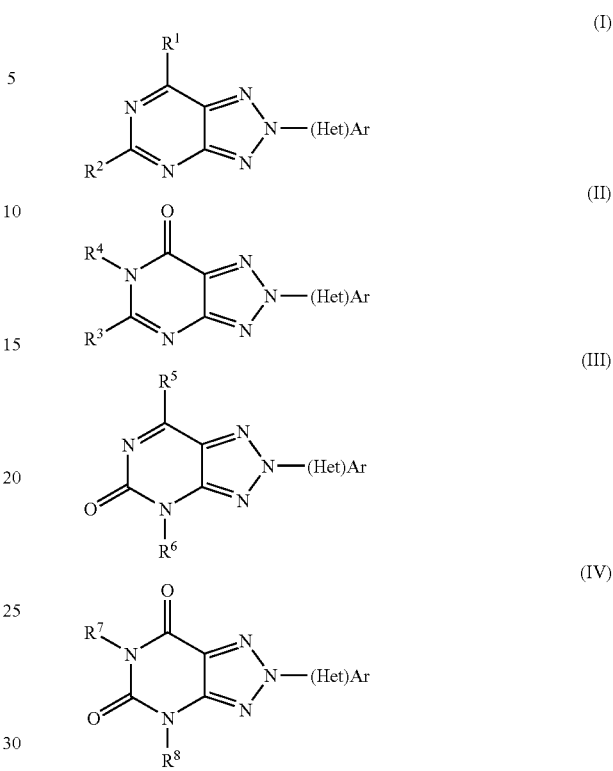

where the symbols have the following meanings:
$R^1$, $R^2$ are each, independently of one another, H, alkyl, aryl, heteroaryl, OH, O-alkyl, O-aryl, halogen or amino, with at least one of the substituents $R^1$ or $R^2$ being OH, O-alkyl, O-aryl, halogen or amino, preferably amino;
$R^3$, $R^5$ are each, independently of one another, H, alkyl, aryl, heteroaryl, OH, O-alkyl, O-aryl, halogen or amino;
$R^4$, $R^6$, $R^7$, $R^8$ are each, independently of one another, H, alkyl, aryl or heteroaryl;
or
$R^3$ and $R^4$ together with the atoms to which they are bound form a 4- to 8-membered ring which may contain further heteroatoms and is saturated or unsaturated and unsubstituted or substituted;
(Het)Ar is aryl or heteroaryl.

DETAILED DESCRIPTION OF THE INVENTION

For the purposes of the present patent application, the terms used below have the following meanings:

The term "aryl" refers to a radical having a basic skeleton of from 6 to 30 carbon atoms, preferably from 6 to 18 carbon atoms, and is made up of an aromatic ring or a plurality of fused aromatic rings. Suitable basic skeletons are, for example, phenyl, naphthyl, anthracenyl or phenanthrenyl. This basic skeleton can be unsubstituted (i.e. all carbon atoms which are substitutable bear hydrogen atoms) or can be substituted on one, more than one or all substitutable positions of the basic skeleton. Suitable substituents are, for example, alkyl radicals, preferably alkyl radicals having from 1 to 8 carbon atoms, particularly preferably methyl, ethyl, i-propyl or t-butyl, aryl radicals, preferably $C_6$-aryl radicals which may in turn by substituted or unsubstituted, styryl radicals, heteroaryl radicals, preferably heteroaryl radicals which contain at least one nitrogen atom, particularly preferably pyridyl radicals, alkenyl radicals, preferably alkenyl radicals containing one double bond, particularly preferably alkenyl radicals containing one double bond and from 1 to 8 carbon atoms, or groups having a donor or acceptor action. For the purposes of the present invention, groups having a donor action are groups having a +I and/or +M effect, and groups having an acceptor action are groups having a −I and/or −M effect. Suitable groups having a donor or acceptor action are halogen radicals, preferably F, Cl, Br, particularly preferably F, alkoxy radicals, carbonyl radicals, ester radicals, amine radicals, amide radicals, $CH_2F$ groups, $CHF_2$ groups, $CF_3$ groups, CN groups, thio groups or SCN groups. The aryl radicals very particularly preferably bear substituents selected from the group consisting of methyl, F, Cl and alkoxy, or the aryl radicals are unsubstituted. The aryl radical is preferably a $C_6$-aryl radical or a naphthyl radical which may optionally be substituted by at least one of the abovementioned substituents. The $C_6$-aryl radical particularly preferably bears none, one or two of the abovementioned substituents, with a single substituent preferably being located in the para position relative to the further point of linkage of the aryl radical and, in the case of two substituents, these are each located in the ortho position relative to the further point of linkage of the aryl radical. The $C_6$-aryl radical is very particularly preferably an unsubstituted phenyl radical. The naphthyl radical is preferably 1-naphthyl or 2-naphthyl.

The term "heteroaryl" refers to heteroaryl radicals which differ from the abovementioned aryl radicals in that at least one carbon atom in the basic skeleton of the aryl radicals is replaced by a heteroatom. Preferred heteroatoms are N, O and S. Very particular preference is given to one or two carbon atoms of the basic skeleton of the aryl radicals being replaced by heteroatoms. The basic skeleton is particularly preferably selected from among systems such as pyridyl, imidazolyl, cyclic esters, cyclic amides and five-membered heteroaromatics such as thienyl, pyrrolyl and furyl. The basic skeleton can be substituted on one, more than one or all substitutable positions of the basic skeleton. Suitable substituents are the same ones which have been mentioned above for aryl. Particular preference is given to thienyl.

The term "alkyl" refers to an alkyl radical having from 1 to 20 carbon atoms, preferably from 1 to 10 carbon atoms, particularly preferably from 1 to 8 carbon atoms, very particularly preferably from 1 to 4 carbon atoms. This alkyl radical can be branched or unbranched and may be interrupted by one or more heteroatoms, preferably N, O or S. Furthermore, the alkyl radical or alkyl group can be a $C_3$-$C_8$-cycloalkyl radical, preferably a $C_5$- or $C_6$-cycloalkyl radical, which may be interrupted by one or more heteroatoms, preferably N, O or S, for example cyclopentyl and cyclohexyl. Furthermore, this alkyl radical can be substituted by one or more of the substituents mentioned for the aryl groups, in particular halogen radicals, preferably F, Cl, Br, particularly preferably F. It is likewise possible for the alkyl radical to bear one or more aryl groups. In this case, all of the abovementioned aryl groups are suitable. The alkyl radicals are particularly preferably selected from the group consisting of methyl, ethyl, i-propyl, n-propyl, i-butyl, n-butyl, t-butyl, sec-butyl, i-pentyl, n-pentyl, sec-pentyl, neo-pentyl, n-hexyl, i-hexyl, sec-hexyl, cyclopentyl and cyclohexyl. Very particular preference is given to methyl, ethyl, i-propyl, t-butyl and n-Hexyl, in particular methyl.

The term "O-alkyl" refers to an alkoxy radical which has the general formula $-OR^9$. $R^9$ is an alkyl radical as has been defined above. O-alkyl is thus particularly preferably O-methyl, O-ethyl, O-$^i$propyl, O-$^t$butyl and O-$^n$hexyl. Very particular preference is given to O-methyl.

The term "O-aryl" refers to an aryloxy radical which has the general formula $-OR^{10}$. $R^{10}$ is an aryl radical as defined above. Very particular preference is given to O-aryl, O-phenyl, with the phenyl radical being unsubstituted.

The term "halogen" preferably refers to a substituent selected from the group consisting of F, Cl and Br. Halogen is particularly preferably Cl or Br, very particularly preferably Cl. The term "amino" refers to an amino group of the formula $NR^{11}R^{12}$. $R^{11}$ and $R^{12}$ are each, independently of one another, H, alkyl, aryl or heteroaryl. Preferred alkyl, aryl and heteroaryl groups have been mentioned above. Very particular preference is given to dimethylamino. Furthermore, $R^{11}$ and $R^{12}$ together with the N atom of the amino group can form a cyclic radical. This is preferably a five- or six-membered cyclic radical. In addition to the nitrogen atom, it can contain one or more further heteroatoms selected from among N, O and S. Very particularly preferred cyclic amino radicals are morpholino, pyrrolidino and piperidino. Very particularly preferred amino groups are dimethylamino, morpholino, pyrrolidino and piperidino.

The term "(Het)Ar" refers to an aryl radical or a heteroaryl radical. Suitable aryl radicals and heteroaryl radicals have been mentioned above. (Het)Ar is preferably a radical of the formula

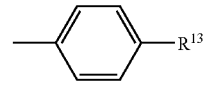

where $R^{13}$ is H, alkyl, O-alkyl, S-alkyl, aryl, O-aryl, S-aryl or alkenylaryl. Here, the terms alkyl, O-alkyl, aryl and O-aryl are as defined above. The radical $R^{13}$ is preferably H, $OCH_3$, phenyl, which may be substituted or unsubstituted, particularly preferably unsubstituted phenyl, or styryl, which is unsubstituted.

The term "S-alkyl" refers to a radical of the general formula S-$R^{14}$. $R^{14}$ is an alkyl radical as has been defined above. S-Alkyl is thus preferably S-methyl, S-ethyl, S-$^i$propyl, S-$^t$butyl and S-$^n$hexyl, particularly preferably S-methyl.

The term "S-aryl" refers to a radical of the general formula S-$R^{15}$. $R^{15}$ is an aryl radical as has been defined above. S-Aryl is thus preferably S-phenyl, with the phenyl radical being unsubstituted.

In a preferred embodiment, the present invention relates to triazole derivatives of the formula I in which $R^1$ is Cl, OH, $OCH_3$, OPh or morpholino, preferably OH or $OCH_3$, Cl or morpholino, particularly preferably Cl or morpholino;

and/or $R^2$ is OH, $OCH_3$, OPh, piperidino, pyrrolidino, morpholino or $N(CH_3)_2$, preferably OH, $N(CH_3)_2$, piperidino, pyrrolidino or morpholino, particularly preferably $N(CH_3)_2$.

In a further preferred embodiment, the present invention relates to triazole derivatives of the formula II or III in which $R^3$, $R^5$ are each, independently of one another, OH, $OCH_3$, OPh, piperidino, pyrrolidino, morpholino or $N(CH_3)_2$, preferably OH, $N(CH_3)_2$, piperidino, pyrrolidino or morpholino;

and/or $R^4$, $R^6$ are each, independently of one another, H, $CH_3$ or phenyl, preferably H.

In a further preferred embodiment, the present invention relates to triazole derivatives of the formula IV in which $R^7$ and $R^8$ are each, independently of one another, H, $CH_3$ or phenyl, preferably $CH_3$.

In a further preferred embodiment, the present invention relates to triazole derivatives of the formula II in which $R^3$ and $R^4$ together with the atoms to which they are bound form a 5- to 7-membered ring which may contain further heteroatoms, preferably selected from among S, N and O, particularly preferably a further N atom, and is saturated or unsaturated, preferably saturated, and is unsubstituted or substituted. The ring particularly preferably has a substituent selected from among alkyl and aryl on the further N atom while the remaining atoms of the ring are unsubstituted (i.e. bear hydrogen atoms).

The compounds of the formula II in which $R^3$ and $R^4$ together with the atoms to which they are bound form a 5- to 7-membered ring particularly preferably have the following structural formulae:

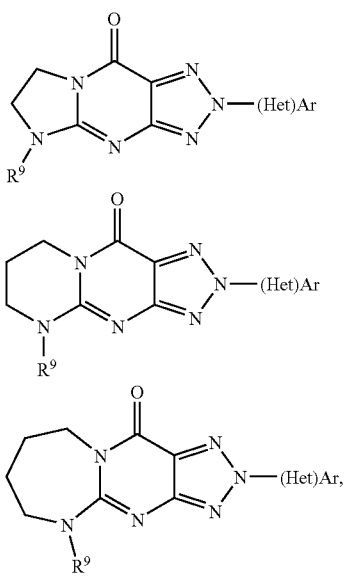

where $R^9$ is alkyl or aryl and (Het)Ar is as defined above. (Het)Ar is preferably

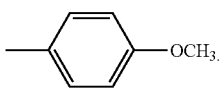

The abovementioned triazole derivatives are very suitable for use in organic light-emitting diodes (OLEDs). The present invention therefore further provides organic light-emitting diodes comprising at least one triazole derivative as defined in the present patent application. The triazole derivatives according to the present patent application are preferably used in the electron-conducting layer or the light-emitting layer as emitter molecules in OLEDs. Particular preference is given to using the triazole derivatives according to the present patent application as emitter molecules in the light-emitting layer of OLEDs.

The abovementioned triazole derivatives used according to the invention can be prepared by methods known to those skilled in the art.

Customary methods are, for example, coupling of suitable amines with suitable diazonium salts and subsequent oxidative ring closure.

Triazole derivatives of the formula I can thus be prepared by the following process:

a) coupling of an amine of the formula V

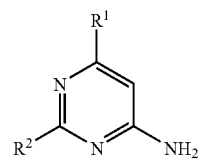

where $R^1$ and $R^2$ are as defined above, with a diazonium salt of the formula VI

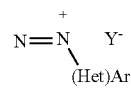

where (Het)Ar is as defined above and $Y^-$ is an anion, to form an azo compound of the formula VII

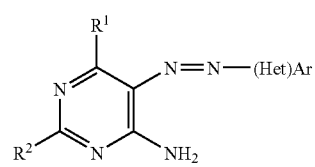

where $R^1$, $R^2$ and (Het)Ar are as defined above;

b) oxidative ring closure of the azo compound of the formula VII to give the desired triazole derivatives of the formula I.

The compounds of the formula II can be obtained by the following process:

a) coupling of an amine of the formula VIII

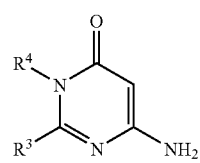

where $R^3$ and $R^4$ are as defined above, with a diazonium salt of the formula VI

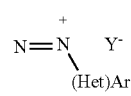

where (Het)Ar is as defined above and $Y^-$ is an anion, to give an azo compound of the formula IX

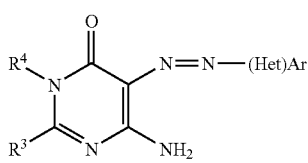

(IX)

where $R^3$, $R^4$ and (Het)Ar are as defined above;

b) oxidative ring closure of the azo compound of the formula IX to give a triazole derivative of the formula II.

The compounds of the formula III can be obtained by the following process:

a) coupling of an amine of the formula X

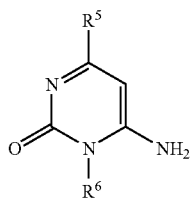

(X)

where $R^5$ and $R^6$ are as defined above, with a diazonium salt of the formula VI

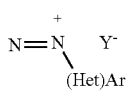

(VI)

where (Het)Ar is as defined above and $Y^-$ is an anion, to give an azo compound of the formula XI

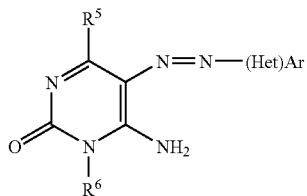

(XI)

where $R^5$ and $R^6$ and (Het)Ar are as defined above.

b) oxidative ring closure of the azu compound of the formula XI to give a triazole derivative of the formula III The compounds of the formula IV can be obtained by the following process:

a) coupling of an amine of the formula XII

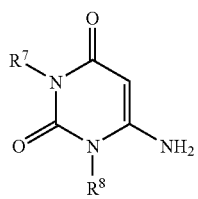

(XII)

where $R^5$ and $R^6$ are as defined above, with a diazonium salt of the formula VI N=N Y⁻
(Het)Ar (VI)

where (Het)Ar is as defined above and $Y^-$ is an anion, to form an azo compound of the formula XIII

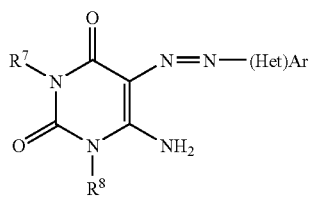

(XIII)

where $R^7$, $R^8$ and (Het)Ar are as defined above;

b) oxidative ring closure of the azo compound of the formula XIII to give a triazole derivative of the formula IV.

Step a)

The amines of the formulae V, VIII, X and XII used as coupling components are known from the literature or can be prepared by methods analogous to those known from the literature, cf. J. Am. Chem. Soc. 73 (1951), 2864, J. Chem. Soc. 1962, 3172, Chem. Pharm. Bull. Japan 13 (1965), 557.

The diazonium salts of the formula VI can be obtained in a customary way by diazotization of the corresponding anilines. These anilines are known or can be prepared by methods analogous to those known to persons skilled in the art, for example from chloronitrobenzenes by reaction with a suitable alcohol and subsequent reduction of the nitro group to an amino group. The anion in the diazonium salts of the formula VI is preferably a halide anion, for example chloride or bromide, a sulfate ion or a tetrafluoroborate ion.

The coupling of an amine of the formula V, VIII, X or XII with a diazonium salt of the formula VI is carried out by methods known to those skilled in the art. The coupling is preferably carried out at a temperature of from −10 to +20° C., particularly preferably from 0 to 10° C.

Step b)

The oxidative ring closure is generally carried out by methods known to those skilled in the art, for example by a method as described in U.S. Pat. No. 2,543,333. The oxidative ring closure can be effected by means of various oxidizing agents. Suitable oxidizing agents are known to those skilled in the art. Examples of suitable oxidizing agents are chromic acid, alkali metal bichromates, hydrogen peroxide, lead tetraacetate, potassium ferricyanide, ferric chloride and copper(II) sulfate.

The oxidative ring closure can be carried out in acidic or basic solvents. In acidic solvents, for example aqueous acetic acid, preference is given to using alkali metal bichromates, hydrogen peroxide or lead tetraacetate as oxidizing agents. In basic solvents, for example pyridine/water mixtures, preference is given to using potassium ferricyanide or copper(II) sulfate. The oxidative ring closure is particularly preferably effected by means of copper(II) sulfate in a pyridine/water mixture. The oxidation using copper(II) salts such as copper (II) sulfate or copper(II) chloride can also be carried out in methanol or methanol/water mixtures in the presence of ammonium or amine salts, e.g. monoalkanolamines or dialkanolamines.

The oxidative ring closure is preferably carried out at a temperature of from 70 to 100° C., particularly preferably from 90 to 100° C.

The triazole derivatives used according to the invention are suitable for use in OLEDs. They are preferably used in the electron transport layer or in the light-emitting layer of an OLED. The triazole derivatives used according to the invention are particularly preferably employed as emitter substances in OLEDs, since they display luminescence (electroluminescence) in the visible region of the electromagnetic spectrum. The triazole derivatives used according to the invention make it possible to provide compounds which display electroluminescence in the red, green and blue regions of the electromagnetic spectrum, depending on their substitution pattern. In particular, it is possible to provide compounds which display electroluminescence both in the blue region and in the blue-green region of the electromagnetic spectrum.

The present invention therefore also provides an organic light-emitting diode (OLED) comprising at least one triazole derivative selected from the group consisting of triazolopyrimidine derivatives and triazolouracil derivatives according to the present patent application. Preferred triazole derivatives selected from the group consisting of triazolopyrimidine derivatives and triazolouracil derivatives have been mentioned above.

Organic light-emitting diodes (OLEDs) are basically made up of a plurality of layers:
1. anode
2. hole transport layer
3. light-emitting layer
4. electron-transport layer
5. cathode The triazole derivatives selected from the group consisting of triazolopyrimidine derivatives and triazolouracil derivatives are preferably used as emitter molecules in the light-emitting layer. The present invention therefore also provides a light-emitting layer comprising at least one triazole derivative selected from the group consisting of triazolopyrimidine derivatives and triazolouracil derivatives. Preferred triazole derivatives selected from the group consisting of triazolopyrimidine derivatives and triazolouracil derivatives have been mentioned above.

The triazole derivatives selected from the group consisting of triazolopyrimidine derivatives and triazolouracil derivatives which are used according to the invention can be present as such, i.e. without further additives, in the light-emitting layer. However, it is likewise possible for further compounds to be present in the light-emitting layer in addition to the triazole derivatives selected from the group consisting of triazolopyrimidine derivatives and triazolouracil derivatives which are used according to the invention. For example, a fluorescent dye can be present in order to alter the emission color of the organic compound used as emitter molecule. Furthermore, a diluent material can be used. This diluent material can be a polymer, for example poly(N-vinylcarbazole) or polysilane. However, the diluent material can likewise be a small molecule, for example 4,4'-N,N'-dicarbazolebiphenyl (CBP) or tertiary aromatic amines. If a diluent material is used, the proportion of triazole derivatives used according to the invention in the light-emitting layer is generally less than 20% by weight, preferably from 3 to 10% by weight. In one embodiment of the present invention, the triazole derivatives selected from the group consisting of triazolopyrimidine derivatives and triazolouracil derivatives which are used according to the invention are used as such, thus avoiding complicated covaporization of the triazole derivatives with a matrix material (diluent material or fluorescent dye). For this purpose, it is essential that the triazole derivatives selected from the group consisting of triazolopyrimidine derivatives and triazolouracil derivatives luminesce as solids. The organic compounds selected from the group consisting of triazolopyrimidine derivatives and triazolouracil derivatives which are used according to the invention display luminescence as solids. Thus, the light-emitting layer in a preferred embodiment comprises at least one triazole derivative selected from the group consisting of triazolopyrimidine derivatives and triazolouracil derivatives and no matrix material selected from among diluent material and fluorescent dye.

The abovementioned individual layers of the OLED can in turn be made up of 2 or more layers. For example, the hole transport layer can be made up of a layer into which holes are injected from the electrode and a layer which transports the holes away from the hole injection layer to the light-emitting layer. The electron transport layer can likewise consist of a plurality of layers, for example a layer into which electrons are injected by the electrode and a layer which receives electrons from the electron injection layer and transports them to the light-emitting layer. These layers are each selected according to factors such as energy level, heat resistance and charge carrier mobility and also energy difference between the layers mentioned and the organic layers or the metal electrodes. A person skilled in the art will be able to select the structure of the OLEDs in such a way that it is optimally matched to the organic compounds used according to the invention as emitter substances.

To obtain particularly efficient OLEDs, the HOMO (highest occupied molecular orbital) of the hole transport layer should be matched to the work function of the anode and the LUMO (lowest unoccupied molecular orbital) of the electron transport layer should be matched to the work function of the cathode.

The present invention further provides an OLED comprising at least one light-emitting layer according to the invention. The further layers in the OLED can be made up of any material which is customarily used in such layers and is known to those skilled in the art.

The anode (1) is an electrode which provides positive charge carriers. It can, for example, be made up of materials comprising a metal, a mixture of various metals, a metal alloy, a metal oxide or a mixture of various metal oxides. As an alternative, the anode can be a conductive polymer. Suitable metals include the metals of groups Ib, IVa, Va and VIa of the Periodic Table of the Elements and the transition metals of group VIII. If the anode is to be transparent to light, use is generally made of mixed metal oxides of groups IIb, IIIb and IVb of the Periodic Table of the Elements, for example indium-tin oxide (ITO). It is likewise possible for the anode (1) to comprise an organic material, for example polyaniline, as described, for example, in Nature, Vol. 357, pages 477 to 479 (Jun. 11, 1992). At least one of the anode or cathode should be at least partially transparent to enable the light produced to be emitted.

Suitable hole transport materials for layer (2) of the OLED of the invention are disclosed, for example, in Kirk-Othmer Encyclopedia of Chemical Technology, 4th edition, Vol. 18, pages 837 to 860, 1996. Both hole-transporting molecules and polymers can be used as hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)(1,1'-biphenyl)-4,4'-diamine (TTB) and porphyrin compounds such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping polymers such as polystyrene and polycarbonate with hole-transporting molecules. Suitable hole-transporting molecules are the molecules mentioned above.

Suitable electron-transporting materials for layer (4) of the OLEDs of the invention comprise metals chelated with oxinoid compounds, e.g. tris(8-quinolinolato)aluminum ($Alq_3$), compounds based on phenanthroline e.g. 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) can serve either to aid electron transport or as a buffer layer or barrier layer to avoid quenching of the exciton at the boundaries of the layers of the OLED. The layer (4) preferably improves the mobility of the electrons and reduces quenching of the exciton.

The cathode (5) is an electrode which serves to introduce electrons or negative charge carriers. The cathode can be any metal or nonmetal which has a lower work function than the anode. Suitable materials for the cathode are selected from the group consisting of alkali metals of group Ia, for example Li, Cs, alkaline earth metals of group IIa, metals of group IIb of the Periodic Table of the Elements including the rare earth metals and the lanthanides and actinides. Metals such as aluminum, indium, calcium, barium, samarium and magnesium and combinations thereof can also be used. Furthermore, lithium-containing organometallic compounds or LiF can also be applied between the organic layer and the cathode to reduce the operating voltage.

The OLED of the present invention can further comprise additional layers which are known to those skilled in the art. For example, a further layer can be applied between the layer (2) and the light-emitting layer (3) in order to aid transport of the positive charge and/or to match the band gap of the layers to one another. As an alternative, this further layer can serve as protective layer. In an analogous way, additional layers can be present between the light-emitting layer (3) and the layer (4) to aid transport of the negative charge and/or to match the band gap between the layers to one another. As an alternative, this layer can serve as protective layer.

In a preferred embodiment, the OLED of the invention contains, in addition to the layers (1) to (5), at least one of the following layers:
 a hole injection layer between the anode (1) and the hole transport layer (2);
 a blocking layer for electrons between the hole transport layer (2) and the light-emitting layer (3);
 a blocking layer for holes between the light-emitting layer (3) and the electron transport layer (4);
 an electron injection layer between the electron transport layer (4) and the cathode (5).

A person skilled in the art will know how to select suitable materials (for example on the basis of electrochemical studies). Suitable materials for the individual layers are known to those skilled in the art and are disclosed, for example, in WO 00/70655.

Furthermore, each of the abovementioned layers of the OLED of the invention can be made up of one or more layers. It is also possible for some or all of the layers (1), (2), (3), (4) and (5) to be surface-treated in order to increase the efficiency of charge carrier transport. The choice of materials for each of the layers mentioned is preferably made so as to obtain an OLED having a high efficiency.

The OLED of the invention can be produced by methods known to those skilled in the art. In general, the OLED is produced by successive vapor deposition of the individual layers on a suitable substrate. Suitable substrates are, for example, glass or polymer films. The vapor deposition can be carried out using customary techniques such as thermal vaporization, chemical vapor deposition and others. In an alternative process, the organic layers can be applied from solutions or dispersions in suitable solvents, with coating techniques known to those skilled in the art being employed.

In general, the various layers have the following thicknesses: anode (2) from 500 to 5000 Å, preferably from 1000 to 2000 Å; hole-transport layer (3) from 50 to 1000 Å, preferably from 200 to 800 Å, light-emitting layer (4) from 10 to 1000 Å, preferably from 100 to 800 Å, electron transport layer (5) from 50 to 1000 Å, preferably from 200 to 800 Å, cathode (6) from 200 to 10 000 Å, preferably from 300 to 5000 Å. The position of the recombination zone of holes and electrons in the OLED of the invention and thus the emission spectrum of the OLED can be influenced by the relative thickness of each layer. This means that the thickness of the electron transport layer should preferably be selected so that the electron/hole recombination zone is located in the light-emitting layer. The ratio of the thicknesses of the individual layers in the OLED is dependent on the materials used. The thicknesses of any additional layers used are known to those skilled in the art.

The use of the triazole derivatives selected from the group consisting of triazolopyrimidine derivatives and triazolouracil derivatives which are used according to the invention in the light-emitting layer of the OLEDs of the invention makes it possible to obtain OLEDs having a high efficiency. The efficiency of the OLEDs of the invention can also be improved by optimizing the other layers. For example, highly efficient cathodes such as Ca, Ba or LiF can be used. Shaped substrates and new hole-transport materials which effect a reduction in the operating voltage or an increase in the quantum efficiency can likewise be used in the OLEDs of the invention. Furthermore, additional layers can be present in the OLEDs to adjust the energy level of the various layers and to aid electroluminescence.

The OLEDs of the invention can be used in all devices in which electroluminescence is useful. Suitable devices are preferably selected from among stationary and mobile VDUs. Stationary VDUs are, for example, VDUs of computers, televisions, VDUs in printers, kitchen appliances and advertising signs, lighting and information signs. Mobile VDUs are, for example, VDUs in mobile telephones, laptops, vehicles and destination displays on buses and trains.

The triazole derivatives selected from the group consisting of triazolopyrimidine derivatives and triazolouracil derivatives which are used according to the invention can also be employed in OLEDs having an inverse structure. In these inverse OLEDs, the triazole derivatives used according to the invention are once again preferably used in the light-emitting layer, particularly preferably as light-emitting layer without further additives. The structure of inverse OLEDs and the materials customarily used therein are known to those skilled in the art.

Some of the abovementioned triazole derivatives of the formulae I, II, III and IV are new compounds which have not been known hitherto from the prior art. The present invention therefore also provides triazole derivatives selected from the group consisting of triazole derivatives of the general formulae I, II, III and IV

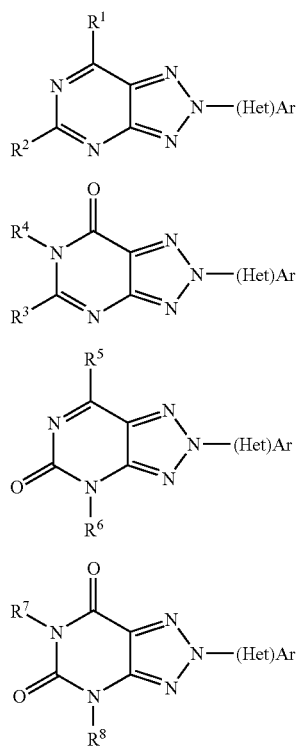

in which the symbols have the following meanings:

$R^1$ is halogen, preferably Cl, or amino, preferably a cyclic amino group, particularly preferably morpholino;

$R^2$ is amino, preferably dimethylamino;

$R^3$, $R^5$ are each, independently of one another, amino, preferably dimethylamino or a cyclic amino group, particularly preferably morpholino, pyrrolidino or piperidino;

$R^4$, $R^6$ are each, independently of one another, H, alkyl, aryl or heteroaryl, preferably H;

$R^7$, $R^8$ are each, independently of one another, H, alkyl, aryl, with $R^7$ and $R^8$ not both being H, preferably alkyl, particularly preferably methyl;

or $R^3$ and $R^4$ together with the atoms to which they are bound form a 5- to 7-membered ring which may contain further heteroatoms, preferably selected from among S, N and O, particularly preferably a further N atom, and is saturated or unsaturated, preferably saturated, and is unsubstituted or substituted. The ring particularly preferably has a substituent selected from among alkyl and aryl on the further N atom while the remaining atoms of the ring are unsubstituted (i.e. bear hydrogen atoms);

(Het)Ar is a radical of the formula

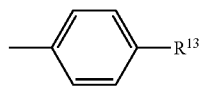

where $R^{13}$ is H, alkyl, O-alkyl, S-alkyl, O-aryl, S-aryl or alkenylaryl, preferably O-alkyl, O-phenyl, phenyl which may be substituted or unsubstituted or styryl which is unsubstituted, particularly preferably O-alkyl or phenyl which is unsubstituted, very particularly preferably in the compounds of the formulae I, II or III O—$CH_3$ or in the compounds of the formula IV O—$CH_3$ or unsubstituted phenyl.

The meanings of the terms alkyl, aryl, heteroaryl, O-alkyl, O-aryl, S-alkyl, S-aryl, halogen and amino have been explained above.

Very particular preference is given to triazole derivatives of the formula I in which (Het)Ar is a radical of the formula

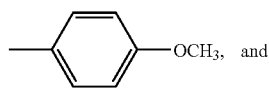

$R^2$ is dimethylamino and $R^1$ is Cl or morpholino.

Furthermore, very particular preference is given to triazole derivatives of the formula II in which (Het)Ar is a radical of the formula

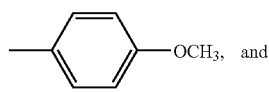

$R^4$ is H and $R^3$ is a radical selected from the group consisting of dimethylamino, morpholino, pyrrolidino and piperidino.

Furthermore, very particular preference is given to triazole derivatives of the formula II which have the following formulae:

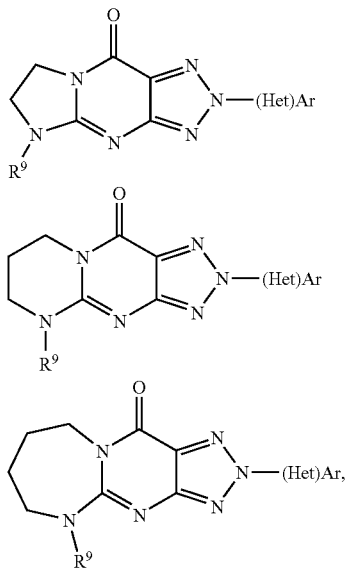

where $R^9$ is alkyl or aryl and (Het)Ar is a radical of the formula

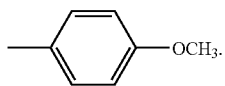

Furthermore, very particular preference is given to triazole derivatives of the formula IV in which (Het)Ar is a radical of the formula

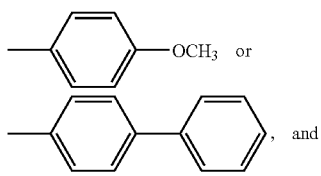

$R^7$ and $R^8$ are each $CH_3$.

The novel triazole derivatives of the formulae I, II, III and IV are suitable for use in OLEDs, preferably for use in the electron-conducting layer or in the light-emitting layer. The abovementioned triazole derivatives of the invention are particularly preferably used as emitter substances in the light-emitting layer in OLEDs. The use of the triazole derivatives of the invention in OLEDs and OLEDs comprising the triazole derivatives of the invention and a light-emitting layer comprising the triazole derivatives of the invention have been described above.

The triazole derivatives of the invention can be prepared by methods known to those skilled in the art. Suitable methods have likewise been described above.

The present invention therefore also provides a process for preparing the novel triazole derivatives of the general formulae I, II, III and IV as mentioned above, which comprises the steps:

a) coupling of an amine of the formula V, VIII, X or XII

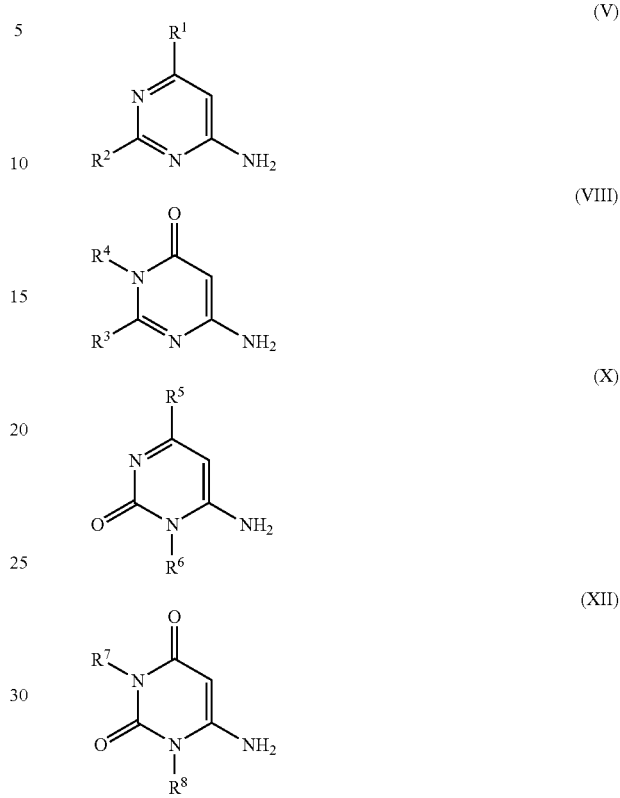

where $R^1$, $R^2$, $R^3$, $R^4$, $R^5$, $R^6$, $R^7$ and $R^8$ are as defined for the triazole derivatives of the invention, with a diazonium salt of the formula VI

where (Het)Ar is as defined for the triazole derivatives of the invention and $Y^-$ is an anion, to give an azo compound of the formula VII, IX, XI or XIII,

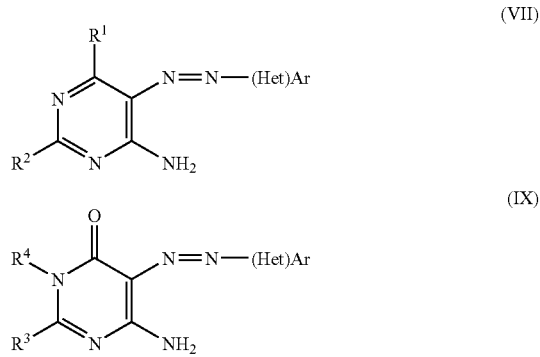

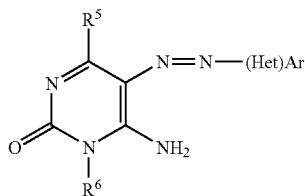

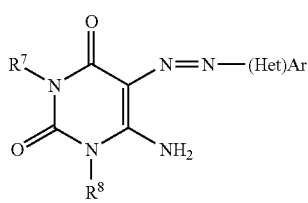

where $R^1$, $R^2$, $R^3$, $R^4$, $R^5$, $R^6$, $R^7$ and $R^8$ and also (Het)Ar are as defined above for the triazole derivatives of the invention;

b) oxidative ring closure of the azo compounds of the formula VII, IX, XI or XIII, to form the corresponding triazole derivatives of the formula I, II, III or IV.

In the diazonium compound of the formula VI, the anion $Y^-$ is preferably a halide such as chloride or bromide, a sulfate ion or a tetrafluoroborate ion.

Suitable reaction conditions for the process steps a) and b) are the same as those described above. The preparation of the starting materials used in steps a) and b) has likewise been described above and is generally carried out by methods analogous to those known to persons skilled in the art.

The following examples illustrate the invention.

EXAMPLES

Example 1

5-Dimethylamino-2-(4-methoxyphenyl)-2H-[1,2,3]triazolo[4,5-d]pyrimidin-7-oe

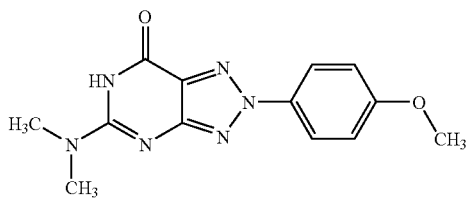

37.5 g (0.30 mol) of 99 pure p-anisidine are suspended in 150 ml of water and 75 g of conc. HCl and cooled to 0-5° C. A solution of 20.7 g (0.30 mol) of sodium nitrite in 50 ml of water is added dropwise over a period of 40 minutes. The reaction solution is stirred at 0-5° C. for another 30 minutes and is subsequently added to a suspension of 46.3 g (0.30 mol) of 6-amino-5-dimethylamino-3H-pyrimidin-4-one and 24.6 g (0.30 mol) of sodium acetate in 460 ml of water. The solution is stirred for 2 hours at 0-5° C. and overnight at room temperature. The precipitate is filtered off with suction, washed with water and dried at 75° C. under reduced pressure. This gives 74.4 g of a red azo dye. This is suspended in 904 ml of pyridine. The suspension is added dropwise over a period of 45 minutes to a solution of 200 g (0.80 mol) of copper(II) sulfate pentahydrate in 904 ml of water which is at a temperature of 70° C. The temperature is subsequently increased to 90-100° C., with the solid firstly dissolving and a yellow-brown precipitate then forming with foaming of the suspension. The suspension is stirred at 100° C. for 15 hours and air is then passed into it for 6 hours. After the reaction solution has cooled, the precipitate is filtered off with suction, washed with water and dried at 75° C. under reduced pressure. This gives 65.6 g of solid. To purify it, a sample is recrystallized twice from dimethylformamide and then sublimed at 250° C. and $3\times10^{-5}$ mbar. This gives an analytically pure, virtually colorless solid which melts at 311-312° C.

UV/Vis (DMSO): $\lambda_{max}$ (lg λ)=348 nm (4.28)

$\lambda_{max,em}$=425 nm

IR(KBr): 1695, 1599, 1566, 1521, 1506, 1434, 1372, 1338, 1279, 1250, 1222, 1169, 963 cm$^{-1}$ $^1$H-NMR (500 MHz; D$_6$-DMSO): 3.13 (s; 6H; N(CH$_3$)$_2$), 3.90 (s; 3H, OCH$_3$), 7.18 (d; 2H, aromatic H), 8.02 (d; 2H, aromatic H), 11.13 (s; 1H)

$^{13}$C-NMR (500 MHz; D$_6$-DMSO): 37.96 (q; N-CH$_3$), 55.64 (q; OCH$_3$), 114.92 (d; phenyl C), 120.00 (d; phenyl C), 127.22 (s; quaternary C=N), 132.84 (s; N-phenyl C), 154.83 (s; quaternary C=N), 157.21 (s; O-phenyl C), 159.51 (s; C—N(CH$_3$)$_2$, C=O)

Example 2

5-Pyrrolidino-2-(4-methoxyphenyl)-2H-[1,2,3]triazolo[4,5-d]pyrimidin-7-one

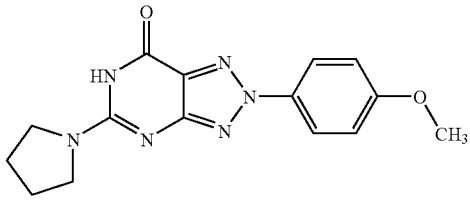

The preparation is carried out by a method analogous to Example 1 using 5.41 g (30 mmol) of 6-amino-5-pyrrolidino-3H-pyrimidin-4-one as starting material. This gives 6.45 g of azo dye which is oxidized to give 4.13 g of triazolopyrimidinol (crude product). To purify this, a sample is recrystallized from dimethylformamide.

Melting point: 329-332° C. (decomposition)

UV/Vis (DMSO): $\lambda_{max}$ (lg λ)=352 nm (4.27)

IR (KBr): 1705, 1691, 1612, 1592, 1565, 1521, 1507, 1458, 1438, 1403, 1248, 1014, 960, 835, 717 cm$^{-1}$

Example 3

5-Piperidino-2-(4-methoxyphenyl)-2H-[1,2,3]triazolo[4,5-d]pyrimidin-7-one

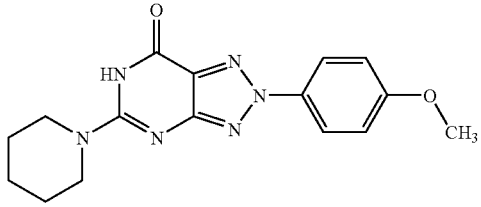

The preparation is carried out by a method analogous to Example 1 using 2.94 g (15 mmol) of 6-amino-5-piperidino-3H-pyrimidin-4-one as starting material. This gives 4.08 g of azo dye which is oxidized to give 3.59 g of triazolopyrimidinol (crude product). To purify this, a sample is recrystallized from dimethylformamide.

Melting point 316-328° C. (decomposition)

UV/Vis (DMSO): $\lambda_{max}$ (lg $\lambda$)=348 nm (4.26)

IR (KBr): 1692, 1609, 1588, 1523, 1507, 1454, 1429, 1410, 1279, 1248, 1179, 1019, 963, 834 cm$^{-1}$

Example 4

5-Morpholino-2-(4-methoxyphenyl)-2H-[1,2,3]triazolo[4,5-d]pyrimidin-7-one

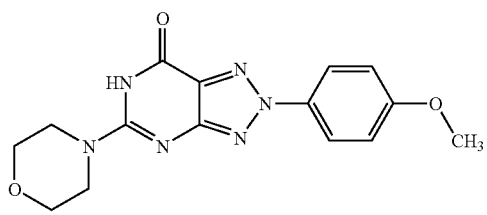

The preparation is carried out by a method analogous to Example 1 using 4.79 g (30 mmol) of 6-amino-5-morpholino-3H-pyrimidin-4-one as starting material. This gives 4.00 g of azo dye which is oxidized to give 1.59 g of triazolopyrimidinol (crude product). To purify this, a sample is recrystallized from dimethylformamide.

Melting point 329-332° C. (decomposition)

UV/Vis (DMSO): $\lambda_{max}$ (lg $\lambda$)=344 nm (4.29)

IR (KBr): 1691, 1609, 1587, 1524, 1507, 1469, 1447, 1369, 1281, 1250, 1116, 1017, 966, 833, 624 cm$^{-1}$

Example 5

7-Chloro-5-dimethylamino-2-(4-methoxyphenyl)-2H-[1,2,3]triazolo[4,5-d]pyrimidine

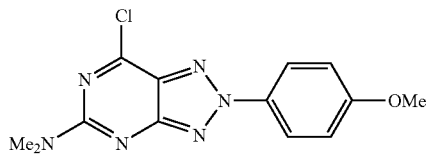

12.5 g (45 mmol) of recrystallized 5-dimethylamino-2-(4-methoxyphenyl)-2H-[1,2,3]-triazolo[4,5-d]pyrimidin-7-ol are slowly introduced into 56 ml of phosphorus oxychloride. The reaction mixture is refluxed for 3 hours. Phosphorus oxychloride is subsequently distilled off. The residue is poured onto ice. The suspension is stirred overnight, filtered with suction, the solid is washed with water and dried at 70° C. under reduced pressure. The crude product (12.39 g) is recrystallized from 150 ml of dioxane. This gives 10.16 g of a yellow solid.

Melting point 208-210° C.

UV/Vis (acetonitrile): $\lambda_{max}$ (lg $\lambda$)=312 (3.99), 400 nm (4.20)

IR (KBr): 1613, 1595, 1566, 1548, 1537, 1507, 1413, 1366, 1258, 1214, 1181, 1042, 1027, 986, 829 cm$^{-1}$ $^1$H-NMR (500 MHz; CF$_3$CO$_2$D): 3.56 (s; 3H; NCH$_3$), 3.70 (s; 3H; NCH$_3$), 4.05 (s; 3H, OCH$_3$), 7.23 (d; 2H, aromatic H), 8.26 (d; 2H, aromatic H)

$^{13}$C-NMR (500 MHz; CF$_3$CO$_2$D): 39.55 (q; N—CH$_3$), 41.50 (q; N—CH$_3$), 57.51 (q; OCH$_3$), 117.44 (d; phenyl C), 124.38 (d; phenyl C), 131.98 (s; quaternary C=N), 134.82 (s; N-phenyl C), 151.49 (s; C—Cl), 154.27 (s; O-phenyl C), 163.35 (s; quaternary C=N), 163.65 (s; C—N(CH$_3$)$_2$)

Example 6

5-Dimethylamino-7-morpholino-2-(4-methoxyphenyl)-2H-[1,2,3]triazolo[4,5-d]pyrimidine

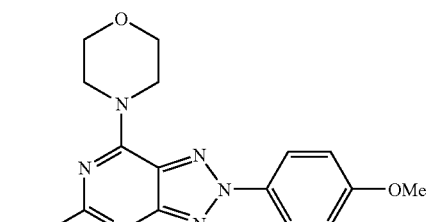

1.73 g (19.9 mmol) of morpholine are added dropwise to a solution of 1.50 g (4.92 mmol) of 7-chloro-5-dimethylamino-2-(4-methoxyphenyl)-2H-[1,2,3]triazolo[4,5-d]pyrimidine in 20 ml of ethanol at room temperature while stirring. After 45 minutes, the solution is admixed with 80 ml of water and stirred for another 3 hours, resulting in formation of a precipitate. This is filtered off with suction, washed with water and dried at 75° C. under reduced pressure. The crude product (1.71 g) is recrystallized twice from 20 ml of dioxane each time. This gives 0.65 g (37%) of a light-yellow powder.

Melting point 220-227° C.

UV/Vis (methylene chloride): $\lambda_{max}$ (lg $\lambda$)=258 (4.34), 290 (4.18), 374 nm (4.28)

(chloroform): $\lambda_{max,em}$=449 nm

IR (KBr): 1583, 1574, 1532, 1506, 1446, 1400, 1388, 1359, 1247, 1230, 1160, 1111, 1021, 967, 835 cm$^{-1}$ $^1$H-NMR (500 MHz; CDCl$_3$): 3.25 (s; 6H; N(CH$_3$)$_2$), 3.88 (s; 3H, OCH$_3$), 3.89 (m; 4H, N—CH$_2$), 4.00 (broad; 2H, O—CH$_2$), 4.40 (broad; 2H, O—CH$_2$), 6.97 (d; 2H, aromatic H), 8.10 (d; 2H, aromatic H)

$^{13}$C-NMR (500 MHz; CDCl$_3$): 37.48 (q; N—CH$_3$), 43.50 (t; N—CH$_2$), 47.50 (t; N—CH$_2$), 55.54 (q; OCH$_3$), 66.88 (t; O—CH$_2$), 114.27 (d; phenyl C), 120.84 (d; phenyl C), 123.60 (s; quaternary C=N), 133.61 (s; N-phenyl C), 153.80 (s; O-phenyl C), 159.51 (s; quaternary C=N), 160.95 (s; morpholino C), 162.23 (s; C—N(CH$_3$)$_2$)

Example 7

2-(4-Methoxyphenyl)4,6-dimethyl-2H-[1,2,3]triazolo[4,5-d]uracil

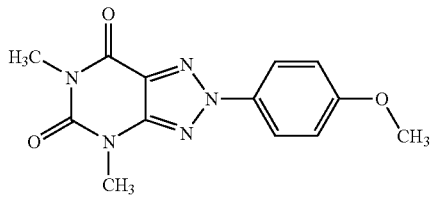

A solution of 11.6 g (46.5 mmol) of copper sulfate pentahydrate in 52.5 ml of water is added dropwise at 70° C. to a solution of 4.34 g (15.0 mmol) of 6-amino-5-(4-methoxyphenylazo)-1,3-dimethyluracil in 52.5 ml pyridine over a period of 45 minutes while stirring. The reaction temperature is subsequently increased to 90-100° C. The reaction solution is stirred at this temperature for 15 hours and air is then passed into it for 6 hours. After the reaction mixture has cooled to room temperature, the precipitate formed is filtered off with suction, washed with water and dried at 75° C. under reduced pressure. The crude product (3.84 g) is recrystallized twice from 50 ml of dioxane each time. 2.23 g (52%) of a colorless solid are isolated.

Melting point 221-223° C.

UV/Vis (methylene chloride): $\lambda_{max}$ (lg $\lambda$)=326 nm (4.35)

(THF): $\lambda_{max,em}$=395 nm

IR (KBr): 1717, 1679, 1611, 1512, 1423, 1415, 1353, 1299, 1263, 1256, 1172, 1059, 1021, 838, 747 cm$^{-1}$ $^1$H-NMR (500 MHz; D$_6$-DMSO): 3.30 (s; 3H; NCH$_3$), 3.50 (s; 3H; NCH$_3$), 3.87 (s; 3H; OCH$_3$), 7.16 (d; 2H, aromatic H), 7.99 (d; 2H, aromatic H)

$^{13}$C-NMR (500 MHz; D$_6$-DMSO): 27.93 (q; N—CH$_3$), 30.59 (q; N—CH$_3$), 55.47 (q; OCH$_3$), 114.79 (d; phenyl C), 120.49 (d; phenyl C), 125.89 (s; quaternary C=N), 132.03 (s; N-phenyl C), 149.71 (s; O-phenyl C), 150.61 (s; C=O), 155.43 (s; C=O), 159.58 (s; quaternary C=N)

Example 8

2-Biphenyl-4-yl-4,6-dimethyl-2H-[1,2,3]triazolo[4,5-d]uracil

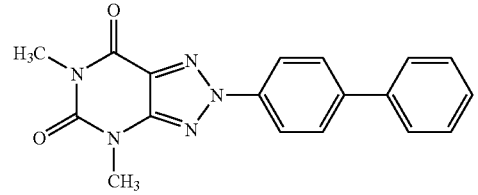

A solution of 47.2 g (189 mmol) of copper sulfate pentahydrate in 210 ml of water is added dropwise at 70° C. to a solution of 20.1 g (60.0 mmol) of 6-amino-5-(biphenyl-4-ylazo)-1,3-dimethyluracil in 210 ml of pyridine over a period of 20 minutes while stirring. The reaction temperature is subsequently increased to 90-100° C. The reaction solution is stirred at this temperature for 16.5 hours and air is then passed into it for 6 hours. After the reaction mixture has cooled to room temperature, the precipitate formed is filtered off with suction, washed with water and dried at 75° C. under reduced pressure. The crude product (14.36 g) is extracted with acetonitrile, resulting in the impurities going into solution. Drying the residue gives 8.18 g (41%) of a yellowish solid.

Melting point 247-250° C.

UV/Vis (methylene chloride): $\lambda_{max}$ (lg $\lambda$)=330 nm (4.50)

(chloroform): $\lambda_{max,em}$=402 nm

IR (KBr): 1723, 1685, 1610, 1603, 1556, 1548, 1522, 1490, 1423, 1414, 1353, 1299, 964, 766, 742 cm$^{-1}$ $^1$H-NMR (500 MHz; CDCl$_3$): 3.45 (s; 3H; NCH$_3$), 3.65 (s; 3H; NCH$_3$), 7.40 (m; 1H, phenyl H), 7.48 (m; 2H, aromatic H), 7.65 (m; 2H, aromatic H), 7.57 (m; 2H, aromatic H), 8.42 (m; 2H, aromatic H)

$^{13}$C-NMR (500 MHz; CDCl$_3$/D$_6$-DMSO): 28.50 (q; N—CH$_3$), 31.03 (q; N—CH$_3$), 119.70 (d; phenyl C), 126.40 (s; quaternary C=N), 126.86 (d; phenyl C), 127.90 (d; phenyl C), 127.94 (d; phenyl C), 128.91 (d; phenyl C), 138.12 (s; N-phenyl C), 139.22 (s; phenyl C), 150.00 (s; C=O), 150.93 (s; C=O), 156.07 (s; quaternary C=N)

The invention claimed is:

1. An organic light-emitting diode comprising at least one compound of the structural formula I:

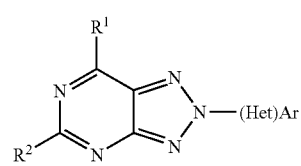

(I)

where the symbols have the following meanings:
R$^1$ is halogen or amino, R$^2$ is amino;
and
(Het) Ar is aryl of the formula

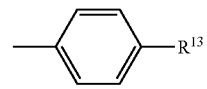

where R$^{13}$ is O-alkyl or aryl.

2. An organic light-emitting diode according to claim 1, wherein the compounds are used as emitter molecules.

3. An organic light-emitting diode according to claim 1, wherein the compounds are used as host molecules in an emitter layer.

4. An organic light-emitting diode comprising a light-emitting layer comprising at least one compound according to claim 1.

* * * * *